United States Patent [19]

Plate et al.

[11] Patent Number: 5,945,457
[45] Date of Patent: *Aug. 31, 1999

[54] PROCESS FOR PREPARING BIOLOGICALLY COMPATIBLE POLYMERS AND THEIR USE IN MEDICAL DEVICES

[75] Inventors: Nicolai A. Plate; Lev I. Valuev; Lubov D. Uzhinova; Vladimir A. Sinani, all of Moscow, Russian Federation

[73] Assignee: A.V. Topchiev Institute of Petrochemical Synthesis, Russian Academy of Science, Moscow, Russian Federation

[*] Notice: This patent issued on a continued prosecution application filed under 37 CFR 1.53(d), and is subject to the twenty year patent term provisions of 35 U.S.C. 154(a)(2).

[21] Appl. No.: 08/942,571

[22] Filed: Oct. 1, 1997

[51] Int. Cl.$^6$ .................. A01N 1/00; A01N 1/02
[52] U.S. Cl. .................. 514/772.1; 514/2; 514/56; 424/422; 424/423; 424/425; 424/426; 427/2.24; 427/2.25; 427/2.26; 523/112; 523/113; 524/916; 526/238.1; 526/238.2; 526/238.23; 526/259; 526/263; 526/271; 526/272; 526/304
[58] Field of Search .................. 523/112, 113; 526/238.1, 238.2, 238.23, 259, 304, 323.1, 312, 313, 320, 324, 325, 262, 318, 263, 307, 321, 318.1, 307.6, 307.7, 318.25, 319, 318.2, 318.3, 271, 272; 514/2; 518/56, 772.1; 424/422; 428/422, 423, 425, 426; 427/2.28, 2.25, 2.26; 528/916

[56] References Cited

U.S. PATENT DOCUMENTS

| | | |
|---|---|---|
| 3,673,612 | 7/1972 | Merrill et al. .................. 3/1 |
| 3,826,678 | 7/1974 | Hoffman et al. . |
| 3,932,656 | 1/1976 | Ramwell et al. .................. 424/423 |
| 3,980,772 | 9/1976 | Ginger et al. .................. 424/94.3 |
| 4,048,064 | 9/1977 | Clark .................. 210/638 |
| 4,331,697 | 5/1982 | Kudo et al. .................. 427/2 |
| 4,582,865 | 4/1986 | Balazs et al. .................. 424/484 |
| 4,615,697 | 10/1986 | Robinson .................. 424/428 |
| 4,678,468 | 7/1987 | Hiroyoshi .................. 424/423 |
| 4,686,288 | 8/1987 | Lormeau et al. .................. 600/285 |
| 4,723,957 | 2/1988 | Magruder et al. .................. 424/629 |
| 4,784,736 | 11/1988 | Lonsdale et al. .................. 523/100 |
| 4,795,436 | 1/1989 | Robinson .................. 424/422 |
| 4,800,016 | 1/1989 | Yang .................. 514/58 |
| 4,861,627 | 8/1989 | Mathiowitz et al. .................. 604/265 |
| 4,867,969 | 9/1989 | Magruder et al. .................. 424/679 |
| 4,904,474 | 2/1990 | Theeuwes et al. .................. 424/424 |
| 4,925,677 | 5/1990 | Feijen .................. 424/484 |
| 4,971,790 | 11/1990 | Magruder et al. .................. 429/78 |
| 4,977,901 | 12/1990 | Ofstead .................. 600/585 |

(List continued on next page.)

FOREIGN PATENT DOCUMENTS

| | | |
|---|---|---|
| 393129 | 8/1991 | Austria . |
| 215941 | 10/1984 | Czechoslovakia . |
| 241262 | 9/1987 | Czechoslovakia . |
| 266851 | 12/1990 | Czechoslovakia . |
| 239062 | 9/1987 | European Pat. Off. . |
| 308235 | 3/1989 | European Pat. Off. . |
| 404558 | 12/1990 | European Pat. Off. . |
| 0 596 615 A1 | 10/1993 | European Pat. Off. . |
| 587715 | 3/1994 | European Pat. Off. . |
| 0596615 | 5/1994 | European Pat. Off. . |
| 687690 | 12/1995 | European Pat. Off. . |
| 702699 | 3/1996 | European Pat. Off. . |
| 3701148 | 7/1987 | Germany . |
| 295178 | 10/1991 | Germany . |
| 85040860 | 9/1985 | Japan . |
| 85040861 | 9/1985 | Japan . |
| 60229933 | 11/1985 | Japan . |
| 61168365 | 7/1986 | Japan . |
| 62038174 | 2/1987 | Japan . |
| 62126107 | 6/1987 | Japan . |

(List continued on next page.)

OTHER PUBLICATIONS

Platé, N.A. and L.I. Valuev (1986). Heparin–Containing Polymeric Materials. Advances in Polymer Science 79, as printed in Biopolymers/Non–Exclusion HPLC. Springer–Verlag, Berlin. pp.96–137.

Grode, G.A., Anderson, S. and R.D. Falb. Studies on the Development of Materials for Use in Artificial Heart Devices. U.S. Government/NTIS, Oct. 30, 1968, Oct. 30, 1969 and Nov. 1, 1971.

Bruck, S.D. (Jan. 1, 1978). Some current problems and new dimensions of polymeric biomaterials for blood–contacting applications. Biomaterials, Medical Devices and Artificial Organs 6 (No. 1): 57–76.

Salyer, I.O. et al. Materials and Components for Circulatory Assist Devices. U.S. Government/NTIS, Jun. 1, 1968.

Fourt, L. Effect of Surfaces on the Blood. U.S. Government/NTIS, Jul. 28, 1966.

Vulic, I. et al. (Jan. 1, 1993). Heparin–containing block copolymers. Part II. In vitro and ex vivo blood compatability. J. Material Sci. Material Med. 4 (No. 5): 448–459.

(List continued on next page.)

Primary Examiner—Frederick Krass
Attorney, Agent, or Firm—Hudak & Shunk Co., L.P.A.; Nestor W. Shust

[57] ABSTRACT

A hemocompatible composition comprising a polymer containing at least one pharmacologic material chemically bonded to a polymer backbone. Such compositions may be obtained by reacting a pharmacologic material with a compound containing a polymerizable group (e.g., an acyl halide) and thereafter either copolymerizing the acylated material with one or more copolymerizable monomers or first irradiating a backbone polymer and thereafter grafting the acylated pharmacologic material onto the irradiated polymer. The resulting products are hemocompatible and may be used in the manufacture of medical devices which come in contact with blood or other bodily fluids. The advantage of chemically bonded pharmacologic materials is that they are not leached out and retain their pharmaceutical effectiveness for a long period of time. The compositions may contain one or more additional pharmacologic materials which are physically admixed with polymers containing bonded pharmacologic materials.

33 Claims, No Drawings

U.S. PATENT DOCUMENTS

| | | | |
|---|---|---|---|
| 4,983,392 | 1/1991 | Robinson | 424/427 |
| 5,001,062 | 3/1991 | Larsson et al. | 623/1 |
| 5,019,649 | 5/1991 | Lormeau et al. | 600/285 |
| 5,047,020 | 9/1991 | Hsu | 536/11 |
| 5,061,738 | 10/1991 | Solomon et al. | |
| 5,135,516 | 8/1992 | Sahatjian et al. | 604/265 |
| 5,138,034 | 8/1992 | Uemura et al. | 530/413 |
| 5,182,317 | 1/1993 | Winters et al. | 523/112 |
| 5,278,200 | 1/1994 | Coury et al. | 530/413 |
| 5,306,250 | 4/1994 | March et al. | 604/58 |
| 5,308,641 | 5/1994 | Cahalan et al. | |
| 5,342,621 | 8/1994 | Eury | 424/423 |
| 5,416,198 | 5/1995 | Anderson et al. | 536/111 |
| 5,417,969 | 5/1995 | Hsu et al. | 424/94.3 |
| 5,437,861 | 8/1995 | Okarma et al. | 424/484 |
| 5,449,382 | 9/1995 | Dayton | 623/1 |
| 5,462,976 | 10/1995 | Matsuda et al. | 522/74 |
| 5,468,505 | 11/1995 | Hubbell et al. | 623/1 |
| 5,516,766 | 5/1996 | Weisz et al. | 514/58 |
| 5,523,096 | 6/1996 | Okarma et al. | 424/484 |
| 5,534,619 | 7/1996 | Wakefield et al. | 530/324 |
| 5,541,167 | 7/1996 | Hsu et al. | 514/56 |
| 5,578,075 | 11/1996 | DAyton | 210/638 |

FOREIGN PATENT DOCUMENTS

| | | |
|---|---|---|
| 62217970 | 9/1987 | Japan . |
| 63105767 | 5/1988 | Japan . |
| 63220878 | 9/1988 | Japan . |
| 63277062 | 11/1988 | Japan . |
| 1080368 | 3/1989 | Japan . |
| 1230369 | 9/1989 | Japan . |
| 1232968 | 9/1989 | Japan . |
| 1262869 | 10/1989 | Japan . |
| 3223377 | 10/1991 | Japan . |
| 4069331 | 3/1992 | Japan . |
| 4092673 | 3/1992 | Japan . |
| 5170845 | 7/1993 | Japan . |
| 5279416 | 10/1993 | Japan . |
| 7069931 | 3/1995 | Japan . |
| 7236690 | 9/1995 | Japan . |
| 8109142 | 4/1996 | Japan . |
| 8131536 | 5/1996 | Japan . |
| 9122224 | 5/1997 | Japan . |
| 1727839 | 4/1992 | United Kingdom . |
| 8700060 | 1/1987 | WIPO . |
| WO 8909069 | 10/1989 | WIPO . |
| WO 9012607 | 11/1990 | WIPO . |
| 9115252 | 10/1991 | WIPO . |
| 9116932 | 11/1991 | WIPO . |
| 9200747 | 1/1992 | WIPO . |
| WO 9212717 | 8/1992 | WIPO . |
| WO 9305793 | 4/1993 | WIPO . |
| WO 9316687 | 9/1993 | WIPO . |
| WO 9414897 | 7/1994 | WIPO . |
| 9521869 | 8/1995 | WIPO . |
| WO 9610428 | 4/1996 | WIPO . |
| 9640822 | 12/1996 | WIPO . |
| WO 9704809 | 2/1997 | WIPO . |

OTHER PUBLICATIONS

Unknown. Research on Hollow Fiber Dialyzer Units. U.S. Government/NTIS, Jun. 30, 1967.

Wendel, H.P. et al. (Jan. 1, 1996). Influence of heparin, heparin plus aprotinin and hirudin on contact activation in a cardiopulmonary bypass model. Proc. 1996 Fifteenth Southern Biomedical Engineering Conference (Cat. No. 96TH8154): 522–525.

Krishnamurti, C. et al. Inhibitory Effects of Lysine Analogues on t–PA Induced Whole Blood Clot Lysis. U.S. Government/NTIS, Jan. 1, 1994.

Unknown. Biocompatability of Polymeric Implantation Devices. 1973–May, 1983, and 1973–Jul. 1982, and Jun. 1983–Apr. 1984, and Jun. 1983–Dec. 1989, and Feb. 1, 1994. (Citations from the Rubber and Plastics Research Association Data Base).

Falb, R.D. et al., Development of Blood–Compatible Polymeric Materials. U.S. Government/NTIS, Jun. 29, 1965.

Crowley, J.P. et al., Development of Blood–Compatible Materials: Heparinized Surfaces and Platelet Protective Agents. U.S. Government/NTIS, Mar. 1, 1976.

Musolf, M.C. and V.D. Hulce. Development of Blood Compatible Silicone Elastomers. U.S. Government/NTIS, Jun. 26, 1968.

Nose, Y. Development of New Concepts in Blood Access Device. U.S. Government/NTIS, Nov. 5, 1973.

Baier, R.E. et al. Interfacial Biophysics of Materials in Contact with Blood. U.S. Government/NTIS, Mar. 1, 1976.

Nose, Y. et al. Development and Evaluation of Cardiac Prostheses. U.S. Government/NTIS, May 1, 1977 and Jun. 15, 1978.

Morra, M. et al. (Jan. 1, 1933). Surface modification of blood contacting polymers by poly(ethyleneoxide). Clin. Mater. 14 (No. 3): 255–265.

Lyman, D.J. et al. The Effect of Chemical Structure and Surface Properties of Synthetic Polymers on the Coagulation of Blood. U.S. Government/NTIS, Jan. 1, 1968.

Unknown (Nov. 1, 1976) and Poirier (Aug. 1, 1975). Flocking of Blood–Contacting Surfaces of Artificial Implant Devices. U.S. Government/NTIS.

Kwiatkowski, G.T. et al. Blood Compatible Polyelectrolytes for Use in Medical Devices. U.S. Government/NTIS, Oct. 1, 1973.

Ishihara, K. et al. (1994). Hemocompatibility on graft copolymers composed of poly(2–methacryloyloxyethyl phosphorylcholine) side chain and poly(n–butyl methacrylate) backbone. J. Biomed. Material Res. 28 (No. 2): 225–232.

Beach, W.F. et al. Microfiber Materials for Growth of Intimal Lining in Circulatory Assist Devices. U.S. Government/NTIS, Jun. 30, 1975.

Kronick, P.L. et al. Fabrication and Characterization of Grafted Hydrogen Coatings for Plastic Heart Assist Devices. U.S. Government/NTIS, Jan. 1, 1974.

Hayashi, K. et al. (1977). Biolized intrathoracic left ventricular assist device (LVAD). Medical Instrumentation 11 (No. 4): 202–207.

Queiroz, A.A.A. et al. Evaluation of the blood compatibility of PTFE grafted films with DMAA using gamma radiation. U.S. Government/NTIS, Jan. 1, 1990.

Kronick, P.L. Fabrication and Characarization of Grafted Hydrogel Coatings Prepared by Active–Hydrogen Techniques for Vascular Devices. U.S. Government/NTIS, Jan. 1, 1979.

Hayashi, K. Report for the Government Industrial Research Institute, Osaka, No. 376, Sep. 1968. Studies on Radiation–Induced Graft Copolymerization to Make Polymer Surfaces Hydrophilic and on Antithrombogenicity of the Surfaces Obtained. U.S. Government/NTIS, Sep. 1, 1988.

Merril, E.W. et al. Pilot Model of an Artificial Kidney: in vivo Studies of Heparinized Hydrogels, Membranes from Heparinized Hydrogels, and a Cellophane Adhesive. U.S. Government/NTIS, Oct. 31, 1971.

Kronick, P.L. Fabrication and Characterization of Grafted Hydrogel Coatings Prepared by Active–Hydrogen Techniques for Heart–Assist Devices. U.S. Government/NTIS, Aug. 25, 1978.

Bishop, E.T. et al. Materials for Use in Blood Pumps and Oxygenators. U.S. Government/NTIS, Nov. 1, 1969.

Sukalac, R.W. et al. Current Status of the Biolized Cardiac Prosthesis. IEEE 1981 Frontiers in Engineering in Health Care Conference: p. 33–36.

Falb, R.D. (1974) Surface–Bonded Heparin. In Polymers in Medicine and Surgery. Eds. R.L. Kronethal, Z. Oser and E. Martin. Polymer Science and Technology 8: 77–86. Plenum Press, NY.

PROCESS FOR PREPARING BIOLOGICALLY COMPATIBLE POLYMERS AND THEIR USE IN MEDICAL DEVICES

BACKGROUND OF THE INVENTION

Synthetic polymeric biomedical materials are widely used in medicine and surgery for many applications, including implantation devices, such as heart valves, vascular grafts, tendons, reinforcing meshes, esophageal prostheses, ureter and gastrointestinal segments, drug-delivery implants, and the like, as well as for complex devices that simulate physiological processes, such as artificial kidney/blood dialysis, artificial lung/blood oxygenation, artificial hearts, artificial pancreas systems, and the like. In many of these applications, the synthetic polymeric materials are in direct contact with blood. Therefore, there has been considerable activity in developing methods for making these materials hemocompatible and preventing or reducing the risk of foreign surface-induced thrombosis.

One approach to solving this problem has been to chemically modify the polymer with one or more compounds that inhibit the blood clotting process. Polymers modified with pyrolytic carbon, hydrophilic monomers and other surface active compounds have been used to inhibit the initial stages of thrombus formation, i.e. adsorption of plasma proteins, including the coagulation proteins, to the polymer surface, followed by activation of contact factors, platelet (thrombocyte) adhesion, aggregation and activation. Modification of polymers with fibrinolytic enzymes, such as urokinase, fibrinolysin (plasmin) and streptokinase has also been reported to inhibit clot (thrombus) formation at the later stages of the coagulation process, i.e. a cascading system in which inactive precursor proteins are activated by the active form of the preceding protein in the cascade, culminating in the formation of a fibrin clot by the thrombin-mediated aggregation of fibrinogen molecules. However, fibrinolytic enzymes are useful for only a short-term increase in hemocompatibility because, when introduced into a living organism, they quickly lose activity due to the action of inhibitors and other denaturing agents in the blood. The natural anticoagulant, heparin has been widely studied as polymer surface modifier for longer term hemocompatibility, because of its physiological stability and high anticoagulant activity, although the presence of heparin on a polymer surface has been reported to increase the adherence of platelets. The mechanism of the anti-coagulant activity of heparin is not well understood.

Several approaches have been used for attaching heparin and other biologically active compounds to polymer surfaces to enhance their hemocompatibility. One method employs modification of a surface, such as an artificial blood vessel, with a polymeric gel incorporating an active compound. For example, heparin can be mechanically incorporated into the structure of a polyvinyl alcohol gel, followed by cross-linking of the heparin molecules using a mixture of glutaraldehyde and formaldehyde. However, the biological activity of the heparin is significantly decreased due to self-crosslinking, with resulting inaccessibility of active sites to blood stream substrates. Ionic immobilization of heparin on polymeric materials, such as by complexing with a quaternary ammonium compound, e.g. tridodecylmethylammonium chloride or benzalkonium chloride, has also been reported. However, the relative weakness of ionic bonds results in leaching of heparin into the blood stream over a period of time, with subsequent loss of activity at the implant surface. Covalent bonding of heparin to polymeric gels and polymer surfaces has also been reported. For example, poly(oxyethyl acrylate) or agarose gels may be activated with cyanogen bromide, followed by reaction of the activated gel with heparin. However, not only is cyanogen bromide toxic, but the activity of the heparin is decreased and only a small amount of heparin is bindable by this method. Other methods of covalently binding heparin to polymer surfaces include the forming of heparin derivatives, such as the acid hydrazide of heparin, silylated heparin, ethyleneimine-heparin, carbodiimide-heparin, a cyanuric chloride heparin adduct, and the like, prior to reaction with the polymer surface. However, again, the activity of the heparin is greatly decreased.

Other reported methods employ radiation-induced graft copolymerization of polymeric materials with biologically active compounds. For example, an unsaturated derivative of the fibrinolytic enzyme, plasmin, was bound to a polymer in this manner. However, at the gamma radiation dose employed, the enzymatic activity of the plasmin was markedly decreased. A similar reduction in enzymatic activity was reported in a method of radiation-induced graft copolymerization with the acid chloride of acrylic or methacrylic acid, followed by treatment of the graft copolymer with an aqueous solution of a serine protease. Heparin, graft copolymerized in this manner, produced a high degree of thrombocyte adhesion when in contact with the blood stream.

In view of the foregoing, there is still a need for biologically compatible, polymers for use as medical devices. In particular, there is a need for polymeric materials that are chemically modified with one or more compounds that inhibit the blood clotting process or compounds that perform other pharmacologic functions. More particularly there is a need for polymeric materials that are chemically modified with biologically active compounds that retain a high level of activity when incorporated into the polymeric material and that exhibit the activity over a long term period of weeks, months or years.

SUMMARY OF THE INVENTION

This invention relates generally to modifications of polymers by covalently bonding one or more biologically active materials, especially pharmacologic materials, onto the polymer backbone to form a biologically compatible polymer. The invention also relates to forming biologically compatible copolymers of monomers and functionalized biologically active compounds. In each case, the biologically active material(s) exhibits a higher level of activity in the modified polymer than has been obtained by previous mechanical, ionic or covalent methods of attachment of such materials to polymers, and the biological activity is retained for an extended period of time by virtue of the stability of the covalent bonding of the material(s) and the polymer.

More specifically, the various embodiments of this invention are directed to the preparation of either hydrophilic or hydrophobic polymer compositions that are hemocompatible. Such biologically active polymer compositions may be prepared from hydrophilic polymers, such as crosslinked hydrogel polymers, or from hydrophobic polymers. The biologically active materials, such as pharmacologic compounds which impart certain desired physiological properties to the polymer, may be incorporated by first functionalizing such pharmacologic compounds with a polymerizable group and then copolymerizing such functionalized compounds with monomer(s) that form hydrophilic polymers, or by grafting such functionalized compounds onto a preformed polymer. Such polymers containing pharmacologic ingredients may be used for various applications where the materials come in contact with blood, especially in medical devices of various types.

It is possible and often preferable that another pharmaceutical material, such as an antibiotic or a protease inhibitor, or the like, may be physically incorporated into the hydrophilic polymers that have been modified with one or more pharmacologic compound(s). Such physical incorporation may be accomplished by any known method. Retention of the compound can be controlled by known means, such as the degree of chemical crosslinking of the modified polymers into which another pharmaceutical is being physically incorporated.

Hydrophobic polymers generally are not hemocompatible per se. However, such polymers may be made hemocompatible and pharmacologically active by first activating the polymers, such as by irradiation, and thereafter grafting functionalized biologically active and hemocompatible material(s) onto the polymer.

The resulting hemocompatible polymer compositions may contain pharmacologic compounds throughout the hydrogel polymer network, especially if the functionalized pharmacologic compounds have been copolymerized with at least one monomer forming a hydrophilic polymer hydrogel. On the other hand, when the pharmacologic compound(s) are grafted onto a polymer, one can select conditions under which the grafting occurs throughout the polymer or only the surface of the polymer The resulting polymer compositions thus contain pharmacologic compounds throughout or only on the surface of the polymer. The desired pharmacologic properties will retain its/their activity over an extended period of time, such as several weeks, preferably at least six months, and often several years. Such resulting biologically active polymer compositions may be employed in the manufacture of prostheses for medical applications such as artificial blood vessels, body implants, catheters, and even bone replacements and the like.

DETAILED DESCRIPTION OF THE INVENTION

One embodiment of this invention is directed to chemically (covalently) bonding a biologically active material, especially a pharmacologic material, to a hydrophilic polymer gel or a hydrophobic polymer such that the physiologic properties of said active material are retained. This may be accomplish by first functionalizing the biologically active material by reacting such a material with a polymerizable group, most practically acyl chloride, and thereafter either copolymerizing the functionalized material with a monomer or a mixture of monomers in the presence of a free radical polymerization initiator to form a hydrophilic polymer, or grafting such a functionalized materials onto a hydrophilic polymer gel or onto a hydrophobic polymer.

Another embodiment of the invention is directed to a method of preparing biologically active polymer compositions which retain their activity over a prolonged time period, comprising (a) preparing a hydrophilic polymer;
(b) functionalizing a pharmacologic material by reacting said material with an acyl halide;
(c) copolymerizing said functionalized material with at least one monomer to form a hydrophilic polymer or grafting said functionalized material onto a preformed hydrophilic or hydrophobic polymer to form a modified polymer; and optionally
(d) physically incorporating one or more pharmaceutical materials into the modified polymer.

Examples of biologically active materials that may be incorporated (either by chemical bonding or by physical incorporation) into a polymer to form a modified polymer include, but are not limited to heparin, hirudin, prostacyclenes and analogs thereof, antithrombogenic agents, steroids, ibuprofen, antimicrobials, antibiotics, tissue plasma activators, rifamycin, monoclonal antibodies, snake venom protein by-products, antifibrosis agents, cyclosporine, and mixtures of these bioactive substances for simultaneous multiple treatments. For certain medical devices comprising the modified polymer, it may be preferable to select a biologically active material that confers a desired property of lubricity on the modified polymeric material. Such compounds are known to those skilled in the art.

Generally, if it is desired that a pharmacologic effect of a particular material be retained for a long period of time (often indefinitely), such pharmacologic material would be chemically bound to the base polymer or copolymerized with other monomers. If it is desired that a pharmacologic material back out of the polymer over a limited period of time, it would be preferable to incorporate it physically with a polymer that already contains one or more physiologic materials already bound to the polymer. An illustrative example of this combination is chemically bonding heparin to a polymer and then physically incorporating into that composition an antibiotic.

Exemplary biologically active materials, especially pharmacologic materials, that may be bonded (by the methods described herein) to hydrophilic or hydrophobic polymers are heparin, a natural blood anti-coagulant; L-lysine; adenine; salicylic acid or other such materials, such as heparin and one or more of the following: a proteolytic enzyme, an antibiotic, an inhibitor of a proteolytic enzyme, or any combination of said biologically active materials. The polymers modified with such pharmacologic active materials are hemocompatible and may be used in a variety of medical applications such as prostheses where the product made from the resulting composition comes in contact with blood. Additionally, the modified hydrophilic polymers may also contain physically incorporated additional pharmaceutical materials which will gradually leach out of the modified polymer composition when in contact with a bodily fluid such as blood.

A practical and convenient method is to dissolve one or more pharmaceutical materials in water and then immerse in this solution a hydrogel polymer that had been previously modified with a biologically active material. Depending on the amount of the pharmaceutical material that one wishes to physically incorporate, the modified polymer may be immersed in the pharmaceutical solution after drying or in a partially hydrated state and may remain in the solution from a few seconds to over a day or even more, but more usually from a few minutes to a few hours. Thereafter the polymer composition is further processed depending on the desired use. It may be first dried or formulated in its hydrated state to prepare a coating. Such methods are known to those skilled in the art.

One class of polymers useful in this invention are desirably water interactive and/or hydrophilic in nature and are of a molecular weight or structure, or have been modified, such that they absorb significant quantities of water and may form hydrogels when placed in contact with water or aqueous media for a period of time sufficient to reach equilibrium with water, but which do not fully dissolve at equilibrium in water. For the purpose of specificity, a hydrogel is defined as a polymer matrix which, when placed in contact with an excess of water, absorbs at least two times its weight of water at equilibrium when exposed to water at room temperature.

Such polymers should preferably be stable themselves and form stable hydrogels in a range of pH conditions ranging from pH 1 to pH 10 and most preferably be stable under pH conditions ranging from at least 3 to 9 without additional protective coatings. However, the particularly desirable stability properties must be tailored to the site of required application, and there may be specific times at which higher or lower stabilities to a particular pH and chemical or biological environment will be most desirable. Thus, there may be situations where susceptibility to degradation at a selected pH or in the presence of a specific enzyme or other degrading agent may be useful in achieving a desired effect. Therefore, the polymers used in this invention must be stable under conditions varying from those exposed to blood in various parts in the body to topical applications for which the therapeutic or bioactive material is intended.

The polymers of the invention may preferably include polymers from the group of homo- and copolymers based on various combinations of the following vinyl monomers: acrylic and methacrylic acids, acrylamide, methacrylamide, hydroxyethylacrylate or methacrylate, vinylpyrrolidones, as well as polyvinylalcohol as made by polymerizing vinylacetate and its co- and terpolymers, polyvinylacetate, its co- and terpolymers with the above listed monomers, 2-acrylamido-2-methyl-propanesulfonic acid (AMPS®) and sulfonated styrene. Very useful are copolymers of the above listed monomers with copolymerizable functional monomers such as acryl or methacryl amide acrylate or methacrylate esters where the ester or amide groups are derived from straight or branched chain alkyl having 1 to 24 carbons, aryl having up to four aromatic rings which may contain alkyl substituents of 1 to 6 carbons; steroidal, sulfates, phosphates or cationic monomers such as N,N-dimethylaminoalkyl(meth)acrylamide, dimethylaminoalkyl (meth)acrylate, (meth)acryloxyalkyltrimethyl-ammonium chloride, (meth)acryloxyalkyldimethylbenzyl ammonium chloride, copolymers of vinyl ethers and maleic anhydrides.

A very useful class of polymers applicable in this invention are the carboxylic monomers such as the olefinically-unsaturated carboxylic acids containing at least one activated carbon-to-carbon olefinic double bond, and at least one carboxyl group; that is, an acid or another functional group which readily converts to an acid containing an olefinic double bond which readily polymerizes because of its presence in the monomer molecule, either in the alpha-beta position with respect to a carboxyl group, —C=C—COOH; or as part of a terminal methylene grouping, $CH_2$=C<. Olefinically-unsaturated acids of this class include such materials as the acrylic acids typified by the acrylic acid itself, alpha-cyano acrylic acid, beta methylacrylic acid (crotonic acid), alpha-phenyl acrylic acid, beta-acryloxy propionic acid, cinnamic acid, p-chloro cinnamic acid, 1-carboxy-4-phenyl butadiene-1,3, itaconic acid, citraconic acid, mesaconic acid, glutaconic acid, aconitic acid, maleic acid, fumaric acid, and tricarboxy ethylene. As used herein, the term "carboxylic acid" includes the polycarboxylic acids and those acid anhydrides, such as maleic anhydride, wherein the anhydride group is formed by the elimination of one molecule of water from two carboxyl groups located on the same carboxylic acid molecule. Maleic anhydride and other acid anhydrides useful herein have the general structure

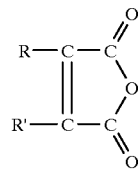

wherein R and R' are selected from the group consisting of hydrogen, halogen and cyanogen (—C≡N) groups and alkyl, aryl, alkaryl, aralkyl, and cycloalkyl groups such as methyl, ethyl, propyl, octyl, decyl, phenyl, tolyl, xylyl, benzyl, cyclohexyl, and the like.

The preferred carboxylic monomers are the monoolefinic acrylic acids having the general structure

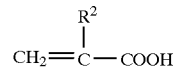

wherein $R^2$ is a substituent selected from the class consisting of hydrogen, halogen, and the cyanogen (—C≡N) groups, monovalent alkyl radicals, monovalent aryl radicals, monovalent aralkyl radicals, monovalent alkaryl radicals and monovalent cycloaliphatic radicals. Of this class, acrylic and methacrylic acid are most preferred. Other useful carboxylic monomers are maleic acid and its anhydride.

The polymers include both homopolymers of carboxylic acids or anhydrides thereof, or the defined carboxylic acids copolymerized with one or more other vinylidene monomers containing at least one terminal >$CH_2$ group. The other vinylidene monomers are present in an amount of less than 30 weight percent based upon the weight of the carboxylic acid or anhydride plus the vinylidene monomer(s). Such monomers include, for example, acrylate ester monomers including those acrylic acid ester monomers such as derivatives of an acrylic acid represented by the formula

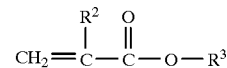

wherein $R^3$ is an alkyl group having from 1 to 30 carbon atoms, preferably 1 to 20 carbon atoms and $R^2$ is hydrogen, methyl or ethyl, present in the copolymer in amount, for example, from about 1 to 40 weight percent or more. Representative acrylates include methyl acrylate, ethyl acrylate, propyl acrylate, isopropyl acrylate, butyl acrylate, isobutyl acrylate, methyl methacrylate, methyl ethacrylate, ethyl methacrylate, octyl acrylate, heptyl acrylate, octyl methacrylate, isopropyl methacrylate, 2-ethylhexyl methacrylate, nonyl acrylate, hexyl acrylate, n-hexyl methacrylate, and the like. Higher alkyl acrylic esters are decyl acrylate, isodecyl methacrylate, lauryl acrylate, stearyl acrylate, behenyl acrylate and melissyl acrylate and methacrylate versions thereof. Mixtures of two or three or more long chain acrylic esters may be successfully polymerized with one of the carboxylic monomers. Other comonomers include olefins, including alpha olefins, vinyl ethers, vinyl esters, and mixtures thereof.

Other vinylidene monomers may also be used, including the acrylic nitriles. The useful α,β-olefinically unsaturated nitriles are preferably the monoolefinically unsaturated nitriles having from 3 to 10 carbon atoms such as acrylonitrile, methacrylonitrile, and the like. Most preferred are acrylonitrile and methacrylonitrile. The amounts used may vary, but for some polymers are, for example from about 1 to 30 weight percent of the total monomers copolymerized. Acrylic amides containing from 3 to 35 carbon atoms including monoolefinically unsaturated amides also may be used. Representative amides include acrylamide, methacrylamide, N-t-butyl acrylamide, N-cyclohexyl acrylamide, higher alkyl amides, where the alkyl group on the nitrogen contains from 8 to 32 carbon atoms, acrylic amides including N-alkylol amides of alpha,beta-olefinically unsaturated carboxylic acids including those having from 4 to 10 carbon atoms such as N-methylol acrylamide, N-propanol acrylamide, N-methylol methacrylamide, N-methylol maleimide, N-methylol maleamic acid esters, N-methylol-p-vinyl benzamide, and the like. Monomers of poly(ethyleneglycol) monomethacrylate of various molecular weights of 50 to 2,000 and monomers of poly(propyleneglycol) monomethacrylate of various molecular weights of 50 to 2,000 may also be used.

Still further useful materials are alpha-olefins containing from 2 to 18 carbon atoms, more preferably from 2 to 8 carbon atoms; dienes containing from 4 to 10 carbon atoms; vinyl esters and allyl esters such as vinyl acetate; vinyl aromatics such as styrene, methyl styrene and chlorostyrene; vinyl and allyl ethers and ketones such as vinyl methyl ether and methyl vinyl ketone; chloroacrylates; cyanoalkyl acrylates such as α-cyanomethyl acrylate, and the α-, β-, and γ-cyanopropyl acrylates; alkoxyacrylates such as methoxy ethyl acrylate; haloacrylates as chloroethyl acrylate; vinyl halides and vinyl chloride, vinylidene chloride and the like; divinyls, diacrylates and other polyfunctional monomers such as divinyl ether, diethylene glycol diacrylate, ethylene glycol dimethacrylate, methylene-bis-acrylamide, allylpentaerythritol, and the like; and bis (β-haloalkyl) alkenyl phosphonates such as bis(β-chloroethyl) vinyl phosphonate and the like as are known to those skilled in the art. Copolymers wherein the carboxy containing monomer is a minor constituent, and the other vinylidene monomers present as major components are readily prepared in accordance with the process of this invention.

Most preferably the hydrogels of the invention should be composed of synthetic copolymers from the group of acrylic and methacrylic acids, acrylamide, methacrylamide, hydroxyethylacrylate (HEA) or methacrylate (HEMA), and vinylpyrrolidones, vinylacetates, vinylethers and anhydrides, which are water interactive and swellable. Specific illustrative examples of useful polymers are the following types:

(meth)acrylamide and 0.1 to 99 wt % (meth)acrylic acid;
(meth)acrylamides and 0.1 to 75 wt % (meth)acryloxyethyl trimethyammonium chloride;
(meth)acrylamide and 0.1 to 75 wt % (meth)acrylamide;
acrylic acid and 0.1 to 75 wt % alkyl(meth)acrylates;
(meth)acrylamide and 0.1 to 75 wt % AMPS® (trademark of Lubrizol Corp.);
(meth)acrylamide and 0 to 30 wt % alkyl(meth)acrylamides and 0.1 to 75 wt % AMPS®;
(meth)acrylamide and 0.1 to 99 wt % HEMA;
(meth)acrylamide and 0.1 to 75 wt % HEMA and 0.1 to 99 wt % (meth)acrylic acid;
(meth)acrylic acid and 0.1 to 99 wt % HEMA;
50 mole % vinyl ether and 50 mole % maleic anhydride;
(meth)acrylamide and 0.1 to 75 wt % (meth)acryloxyalky dimethyl benzylammonium chloride;
(meth)acrylamide and 0.1 to 99 wt % vinyl pyrrolidone;
(meth)acrylamide and 50 wt % vinyl pyrrolidone and 0.1 to 99.9 wt % (meth)acrylic acid;
(meth)acrylic acid and 0.1 to 75 wt % AMPS® and 0.1 to 75 wt % alkyl(meth)acrylamide.

In the above examples, alkyl means $C_1$ to $C_{30}$, preferably $C_1$ to $C_{22}$, linear and branched and $C_4$ to $C_{16}$ cyclic; where (meth) is used, it means that the monomers with and without the methyl group are included.

Representative polymers and the combinations of monomers possessing hydrophilic properties necessary to make synthetic hydrogel polymers are known to those skilled in the art. Some representative examples are disclosed in Scott et al., Handbook of Common Polymers, CRC Press, Cleveland, Ohio (1989, 3rd Ed.).

Synthetic hydrogel polymers may be made by an infinite combination of several monomers in several ratios. In this instance the properties of the final hydrogel composition of this invention is the key parameter. The hydrogel can be crosslinked and it possesses the ability to imbibe and absorb fluid and swell or expand to an enlarged equilibrium state. The hydrogel is a polymeric composition and it swells or expands absorbing at least 2 to 1000 fold its weight of water. The preferred level of water absorption for such hydrogels is 2 to 500 fold its weight of water, whereas the most preferred range of water absorption is 3 to 100 times the weight of the dry polymer. Generally the optimum degree of swellability for a given hydrogel must be separately determined depending on the desired physical property of the final material and on the type of a pharmaceutical that one desires to physically incorporate into the composition. This will depend on the molecular weight, size, solubility and diffusivity of each entrapped therapeutic and the specific spacing and cooperative chain motion associated with each individual polymer.

The hydrophilic polymers useful in this invention are water insoluble but water swellable. It is convenient to refer to such water swollen polymers as hydrogels or gels. Such gels may be conveniently produced from water soluble polymer by the process of crosslinking the polymers by a suitable crosslinking agent. However, stable hydrogels may also be formed from specific polymers under defined conditions of pH, temperature and/or ionic concentration. It is required for this invention that a hydrogel stable under physiologically useful conditions be formed, regardless of the means by which its stability is achieved. Preferably the polymers are crosslinked, that is, crosslinked to the extent that the polymers possess good hydrophilic properties, have improved physical integrity (as compared to the non crosslinked polymers of the same or similar type) and exhibit improved ability to retain within the gel network both the enzyme inhibitor and the therapeutic material or materials, while retaining the ability to release the therapeutic material at the appropriate location and time.

Generally the hydrogel polymers should be crosslinked with a difunctional crosslinking in the amount of from 0.01 to 25 weight percent, based on the weight of the monomers forming the copolymer, and more preferably from 0.1 to 20 weight percent and more often from 0.1 to 15 weight percent of the crosslinking agent. Another useful amount of a crosslinking agent is 0.1 to 10 weight percent. Tri, tetra or higher multifunctional crosslinking agents may also be employed. When such reagents are utilized, lower amounts may be required to attain equivalent crosslinking density.

The crosslinks can be covalent, ionic or hydrogen bonds with the polymer possessing the ability to swell in the presence of water containing fluids. Such crosslinkers and crosslinking reactions are known to those skilled in the art and in many cases are dependent upon the polymer system. Thus a crosslinked network may be formed by free radical copolymerization of unsaturated monomers. Polymeric hydrogels may also be formed by crosslinking preformed polymers by reacting functional groups found on the polymers such as alcohols, acids, amines with such groups as glyoxal, formaldehyde or glutaraldehyde, bis anhydrides and the like.

The polymers also may be crosslinked with any polyene, e.g. decadiene or trivinyl cyclohexane; acrylamides, such as N,N-methylene-bis (acrylamide); polyfunctional acrylates, such as trimethylol propane triacrylate; or polyfunctional vinylidene monomer containing at least 2 terminal $CH_2<$ groups, including, for example, divinyl benzene, divinyl naphthalene, allyl acrylates and the like. Particularly useful crosslinking monomers for use in preparing the copolymers are polyalkenyl polyethers having more than one alkenyl ether grouping per molecule. The most useful possess alkenyl groups in which an olefinic double bond is present attached to a terminal methylene grouping, $CH_2=C<$. They are made by the etherification of a polyhydric alcohol containing at least 2 carbon atoms and at least 2 hydroxyl groups. Compounds of this class may be produced by reacting an alkenyl halide, such as allyl chloride or allyl bromide, with a strongly alkaline aqueous solution of one or more polyhydric alcohols. The product may be a complex mixture of polyethers with varying numbers of ether groups. Analysis reveals the average number of ether groupings on each molecule. Efficiency of the polyether crosslinking agent increases with the number of potentially polymerizable groups on the molecule. It is preferred to utilize polyethers containing an average of two or more alkenyl ether groupings per molecule. Other crosslinking monomers include for example, diallyl esters, dimethallyl ethers, allyl or methallyl acrylates and acrylamides, tetravinyl silane, polyalkenyl methanes, diacrylates, and dimethacrylates, divinyl compounds such as divinyl benzene, polyallyl phosphate, diallyloxy compounds and phosphite esters and the like. Typical agents are allyl pentaerythritol, allyl sucrose, trimethylolpropane triacrylate, 1,6-hexanediol diacrylate, trimethylolpropane diallyl ether, pentaerythritol triacrylate, tetramethylene dimethacrylate, ethylene diacrylate, ethylene dimethacrylate, triethylene glycol dimethacrylate, and the like. Allyl pentaerythritol, trimethylolpropane diallylether and allyl sucrose provide excellent polymers. When the crosslinking agent is present, the polymeric mixtures usually contain up to about 5% or more by weight of crosslinking monomer based on the total of carboxylic acid monomer, plus other monomers, if present, and more preferably about 0.01 to 20 weight percent. A preferred crosslinking agent is alkylene N,N-bis (acrylamide), especially where the alkylene group is methylene or ethylene.

Gels may also be prepared from oligomeric hydrophilic polymer precursors, such as functionalized polyethylene glycol (PEG), polypropylene glycol (PPG) or copolymers of the two (block or random) where either one or both end groups are functionalities that can be polymerized or otherwise incorporated into a polymer. A mono-functionalized group may be incorporated into a polymer to give a side chain of PEG or PPG. A difunctional (or higher) functionalized oligomer can give a blocky construction to a polymer and act as a crosslinker.

Inclusion of PEG and PPG containing polymers (otherwise without functional end groups) during the polymerization of other hydrophilic monomers, such as acrylic acid, methacrylic acid and HEMA, will also create what are known as interpolymers where hydrogen bonding and other types of interactions intimately mix and bond the two separate polymers into a hydrophilic gel.

Crosslinking can be covalent, ionic or hydrogen bonding with the polymer possessing the ability to gel in the presence of water containing fluids.

Crosslinking is used to define the mechanism of association of the polymers in order to form a network that is not easily disrupted and may therefore be viewed as a gel material. There are several mechanisms of forming a crosslink between polymers that are known to those skilled in the art and in many cases are dependent upon the polymer system. Thus the crosslinking in the described systems may be chemical in nature or may be associative in nature. Examples of chemical crosslinking is when a covalent, or ionic bond is established between polymer chains. Addition of multivalent ions into polymer solutions with ionizable side groups will create crosslinking sites. A covalently crosslinked network may be formed by polymerization of monomers with a multiplicity of reactive groups. Covalent network gels may also be formed by crosslinking preformed polymers by reacting functional groups found on the polymers such as alcohols, acids, amines with multifunctional agents such as dialdehydes, multi-epoxides, dianhydrides, multi-isocyanates and the like.

Associative types of crosslinking may be formed through hydrophobic association, and van der Waals association of non-polar groups of a polymer in polar solutions. Hydrogen bonding between polymer groups will also form crosslinked network gels. Associative type crosslinking may be reversible as seen in polymers which demonstrate a lower critical solution temperature (LCST) or an upper critical solution temperature (UCST) where the solubility of portions (or all) of the polymer change due to an external stimulus such as temperature. Interpolymer networks may also display associative crosslinking between groups that have high hydrogen bonding such as that displayed between acid and alcohol or pyrrolidone side groups and the LCST, UCST. Associative crosslinking may also be formed by crystalline association which will reduce the solubility of part of (or all) of the polymer in solution.

Both associative and covalent crosslinking are known to those skilled in the art and may be applied to create hydrogel networks which swell but do not readily dissolve. Reversible associative crosslinking induced by an external stimuli such as temperature, pH, solvent polarity or ionic strength is also considered within the definition of crosslinking. One measure of the existing of crosslinking is the increase of viscosity of the polymer dispersion over that of a non-crosslinked system.

A feature of this embodiment is to prepare hydrogels which have been modified with different biologically active materials. The differently modified polymers could be used together, such as using one composition on the inside of a medical device, such as a catheter, a drain tubing or other devices that require certain pharmacologic properties and a different composition on the outside of a device. Another feature of this embodiment is to prepare polymeric hydrogels that are tubular and that themselves constitute a medical device that can serve, for example, as a drain for bodily fluids. Such a tubular polymeric hydrogel can be modified on the outer surface with biologically active materials having certain pharmacologic properties, and on the inner surface with biologically active materials of a different composition. More specifically, in designing an improved conduit for draining fluid from a body cavity, it may be necessary to control different medical situations relative to the tissue which comes in contact with the outside of the conduit and the fluid that is being drained through the inside of the conduit. For example, such a conduit may be used for draining an exudate from the abdominal cavity in the treatment of peritonitis. In such a situation, it may be desirable to fight or prevent infection and/or to minimize bleeding in the tissues coming in contact with the outside of the conduit. It may also be desirable to improve the outflow of the exudate from the abdominal cavity and prevent closure of such a drain by clogging due to thick masses of proteins, blood and other substances that may be in the exudate. It may also be desirable to inhibit or kill infectious organisms in the exudate. For these purposes, according to this invention, it may be useful to modify the inside of polymeric hydrogel drain, or a polymeric hydrogel coming in contact with the inside of a conduit, with heparin and an antibiotic and possibly also a proteolytic enzyme. The outer side of the conduit may have different requirements and therefore the hydrogel polymer may have to be modified with different pharmacologic materials, such as an antibiotic and/or an inhibitor of proteolytic enzymes.

When it is desirable to coat a surface (which may be a metal or a polymer) any known technique may be employed, such as spray coating, dip coating, roll coating, film (draw) coating and the like. If the surface of a device is a polymer coating, it may be accomplished by first activating the surface (e.g. by irradiation) and then grafting a modified (e.g. acylated) pharmacologic material onto the polymer surface. If the pharmacologic material is already bonded to a polymer, it can be coated onto any surface including a metal or a polymer. The surface may need to be appropriately prepared to accept the polymer containing a pharmacologic material. It is apparent to those skilled in the art that a hydrogel formulation can be modified to improve its frictional properties.

Any combination of biologically active materials may be used to modify hydrogel polymers which have the same or different polymer compositions. Then such differently modified hydrogel polymers may be used in different devices or in different parts of a device or on different surfaces of a part or a device. In practical terms, it may be necessary to make a device or a part from a material such as a metal or a polymer that has hydrophobic property and then coating the desired surfaces with the most appropriately modified polymeric hydrogel by a technique that is well known in the art. The devices made from or coated with the polymers of this invention containing at least one pharmacologic material are particularly useful in mammals where a medical device coming in contact with mammalian tissue must possess certain desirable pharmacologic properties.

The determination as to the use of specific modifiers and the preferred amount used will be obvious to the medically trained and those skilled in the art of manufacturing such devices. For example, it may be useful to incorporate heparin as an anti-coagulant in a polymeric hydrogel. Heparin is a natural sulfated glycosaminoglycan consisting largely of alternating O- or N-sulfated hexuronic acid (D-glucuronic or L-iduronic) and D-glucosamine residues. A key feature of heparin is its heterogeneity. The molecular weight of commercial (mucosal) heparin ranges typically from 3,000 to 25,000 with an average of 15,000. It is possible to prepare higher and lower molecular weight heparin which may display different activity depending upon the fraction isolated. The heparin used in the context of this invention may be any of the materials one can isolate by known methods, and any fractions thereof. These fractions may display different characteristics, such as antithrombin II affinity, anticoagulant action, thrombin inactivation, anti-Xa activity and interaction with other parts of the coagulation cascade. To prepare the modified biologically compatible polymeric hydrogels of the invention, it may be useful employ heparin in the amount of 0.005 wt % to 75 wt % based on the weight of the monomers initially used to form the polymer, preferably 0.05 wt % to 50 wt % and, more preferably 0.1 wt % to 30 wt %.

It may be useful to incorporate (chemically or physically) an enzyme in the biologically compatible polymeric hydrogels of the invention. Any natural or synthetic enzyme may be used including, but not limited to, proteolytic enzymes, such as trypsin, chymotrypsin, pepsin, papain, serine proteases, peptidases, such as carboxypeptidase A, carboxypeptidase B and leucine aminopeptidase, elastase, esterases, subtilisin, lysozyme, urokinase, urease, streptokinase, phosphatases, nucleases, and the like, and further including other enzymes, such as lipases and glucosidases, and the like. For example, it may be useful to employ trypsin in the amount of 0.005 wt % to 20 wt % based on the weight of the monomers initially used to form the polymer, preferably 0.01 wt % to 15 wt % and, more preferably 0.05 wt % to 12 wt %.

It may be useful to incorporate an inhibitor of a proteolytic enzyme in the biologically compatible polymeric hydrogels of the invention. Natural and synthetic inhibitors of proteolytic and other enzymes are known to those skilled in the art. For example, inhibitors of the enzyme, trypsin, include a natural pancreatic trypsin inhibitor, kallikrein, which also inhibits plasmin, chymotrypsin and various other intracellular proteases. It may be useful employ the proteolytic enzyme inhibitor in the amount of 0.005 wt % to 20 wt % based on the weight of the monomers initially used to form the polymer, preferably 0.01 wt % to 15 wt % and, more preferably 0.05 wt % to 12 wt %.

Antibiotics, known to those skilled in the medical arts and including natural and synthetic antibiotics, such as those selected from aminoglycosides, cephalosporins, macrolides, monobactams, penicillins, tetracyclines, and the like, and combinations of these, may be incorporated into the biologically compatible polymeric hydrogels of the invention. For example, it may be useful to employ an antibiotic in the amount of $1 \times 10^{-8}$ wt % to 1 wt % based on the weight of the monomers initially used to form the polymer, preferably $1 \times 10^{-5}$ wt % to 1 wt % and, more preferably, $1 \times 10^{-4}$ wt % to 1 wt %.

It may be useful to incorporate other compounds, such as derivatives of basic amino acids and proteases, into the polymeric hydrogels of the invention. For example, derivatives of the L forms of lysine, arginine, hydroxylysine or histidine may be employed. The presence of the derivative, preferably a derivative of L-lysine, in the polymer matrix favors the adsorption from plasma or blood, of the proenzyme plasminogen which is the inactive precursor of plasmin. Plasmin is an enzyme that is capable of lysis of fibrin clots as they form. The activation of plasminogen to form plasmin is schematically illustrated, as follows:

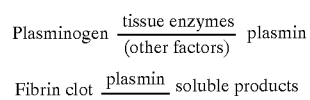

Plasminogen is transformed to plasmin by proteolysis, the cleavage of a single arginyl-valyl bond, resulting in a two-chain molecule held together by a single disulfide bond. Enzymes that are effective proteases in this process include, but are not limited to, tissue-derived enzymes, such as urokinase and trypsin, and bacterial enzymes, such as streptokinase.

The simultaneous presence of an adsorbent for plasminogen, such as an L-lysine derivative, and a protease, such as trypsin, both covalently bound to the polymeric gel matrix allows the continuous adsorbing and cleavage of the proenzyme molecules and the lysis of forming clots such that the activity of the hydrogel is self-renewing and continuous. The result is that the composition has a long term effect of dissolving blood clots.

Thus, it may be useful to incorporate into the polymeric hydrogel both a derivative of a basic amino acid and any protease that effects the transformation of plasminogen to plasmin. For example, trypsin, in the amounts indicated above, and L-lysine, in the amount of 0.5 wt % to 2.5 wt % of weight of the monomers initially used to form the polymer, preferably 0.65 wt % to 2.3 wt % and, more preferably, 0.75 wt % to 2.0 wt %, may be incorporated into the polymeric hydrogel.

The presence of an amino acid such as L-lysine or adenine favors the sorption of profibrinolysin (an inactive precursor of fibrinolysin). When a proteolytic enzyme inhibitor such as trypsin is also present (usually in the amount of 0.1 to 1.5 and preferably 0.3 to 0.8 weight % of the polymer composition), fibrinolysin is activated. If the trypsin is bound with an amino acid to the backbone polymer, a long term activation system is obtained resulting in a long term effect of dissolving clots.

It may also be useful to incorporate into the polymeric hydrogel, compounds that inhibit the aggregation of platelets on the surface of the medical device. For example, derivatives of salicylic acid or adenine are known to perform this function. A further description of compounds such as these, for use in the biologically compatible polymers of the invention, is given below.

Another embodiment of the invention deals with the modification of polymers that are not hemocompatible so that they become hemocompatible. Generally, such polymers are modified with one or more biologically active materials by creating sites on the polymer and then introducing functionalized biologically active material(s). Thus, one way of obtaining a hemocompatible surface from non-hemocompatible polymers is, for example, to irradiate a polymer such as polyethylene film and then to immerse the irradiated film in an aqueous solution of a biologically active material (such as heparin, trypsin or another enzyme, or an enzyme inhibitor, a platelet aggregation inhibitor, and the like) which previously had been functionalized as described above (such as reacting the material with an acryloyl chloride).

Another method of grafting a pharmacologic material to the surface of a backbone polymer is to prepare the surface to react with a polymerizable group such as an acryloyl, e.g. by irradiation) and thereafter grafting a pharmacologic material by reacting said material with the acryl halide group bound to the surface of the polymer substrate.

Polymers which may be modified according to this invention are well known polymers that are obtained by addition or condensation polymerization. Illustrative examples of the various classes of polymers are polymers from vinyl monomers such as polyolefins which include polyethylene, polypropylene, polybutene, ethylene-propylene and other olefin copolymers, copolymers of an olefin and a diene; vinyl acetate homopolymers and copolymers with such comonomers as butyl acrylate, 2-ethylhexyl acrylate, diethyl fumarate, diethylmaleate and vinyl esters of fatty acids or polyvinyl alcohol; polyacrylates which ere discussed in detail above and the like. Also, useful polymers are various condensation polymers such as polyethers, polyesters, polyureas including urea-formaldehyde polymers, polyamides which include a variety of nylons, organosilicon rubbers and others, the above illustrated polymers and methods of their preparation are well known in the art.

An important aspect of this invention is to enable one to design pharmacologic compositions which provide the desired long term activity. For example, it may be useful to bond to a polymer a combination of one or more physiologic materials such as trypsin and lysine or heparin and trypsin.

Generally speaking, the pharmacologic material is first functionalized. That is, an appropriate reactive group is chemically added to the material, most often an ethylenic polymerizable group, and the functionalized material is then copolymerized with monomers and a crosslinking agent using a standard polymerization method such as solution polymerization (usually in water), emulsion, suspension or dispersion polymerization. More specifically, the functionalization agent should have a high enough concentration of functional or polymerizable groups to insure that several sites on the inhibitor are functionalized. After functionalization, the functionalized physiologic material is mixed with the monomers and a crosslinking agent which comprise the reagents from which the polymer gel is formed. Polymerization is then induced in this medium to create a polymeric gel containing the bound material. The gel is then washed with water or other appropriate solvents and otherwise purified to remove trace unreacted impurities and, if necessary, ground or broken up by physical means such as by stirring, forcing it through a mesh, ultrasonification or other suitable means to the preferred particle size. The solvent, usually water, is then removed in such a manner as to not affect the pharmacologic material. A more detailed description of the above described method is given below.

In functionalizing a pharmacologic material the object is to introduce a functional group onto the surface of such material that can subsequently react in polymerization or otherwise couple the material to a polymer such as the hydrogel. As examples of introducing polymerizable groups one may react available amino, hydroxyl carboxyl and thiol groups from the pharmacologic material, with electrophiles containing unsaturated groups or by reacting a pharmacologic material with an unsaturated compound containing an electraphilic group capable of covalently reacting with hydroxyl, amino, carboxyl or thiol groups. For example, unsaturated monomers containing N-hydroxy succinimidyl groups, active carbonates such as p-nitrophenyl carbonate, trichlorophenyl carbonates, tresylate, oxycarbonylimidazoles, epoxide, isocyanates and aldehyde, and unsaturated carboxymethyl azides and unsaturated orthopyridyl-disulfide belong to this category of reagents. Illustrative examples of unsaturated reagents are allylglycidyl ether, allyl chloride, allylbromide, allyl iodide, acryloyl chloride, allyl isocyanate, allylsulfonyl chloride, maleic anhydride, copolymers of maleic anhydride and allyl ether and the like.

All of the amino reactive coupling agent, except aldehyde, can generally react with other amino acids such as imidazole groups of histidine and hydroxyl groups of tyrosine and the thiol groups of cystine of pharmacologic materials if the local environment enhances nucleophilicity of these groups. Aldehyde containing functionalizing reagents are specific to amines. These types of coupling reactions with available groups from lysines, cystines, tyrosine have been extensively documented in the literature and are known to those skilled in the art.

Biologically active agents, such as those described above (e.g. heparin, trypsin, salicylic acid, adenine, lysine) that are immobilized onto the surface of a preformed plastic article or film, may be employed in an amount expressed as the amount of the agent per the surface area (mg/cm$^2$) of the article to which the agent is bonded. For example, it may be useful to employ salicylic acid, adenine, heparin, or trypsin in the amount of $1\times10^{-8}$ mg/cm$^2$ to 1 mg/cm$^2$ of the article. Preferably, the amount is $1\times10^{-5}$ mg/cm$^2$ and, more preferably, $1\times10^{-4}$ mg/cm$^2$ to 1 mg/cm$^2$ of the article.

General Procedure for Functionalization of Pharmacologic Material

In a 20 ml reaction flask, 10 ml of a NaHCO$_3$ buffer solution at pH 8 is stirred. 0.0033 mmole of a pharmacologic material is added and dissolved with agitation. Acryloyl chloride (0.125 mmol) is added to this solution at 4° C. and stirred until the reaction is complete.

General Procedure for the Preparation of Polymer

To the solution obtained in the above functionalization procedure is added the polymerizable monomer (1.4 mmol) and crosslinker (0.65 mmol). This solution is placed under an inert atmosphere. To this solution 0.004 mmol of (NH$_4$)$_2$S$_2$O$_8$ and 0.066 mmol of TMEDA (tetramethylethylenediamine) are added to initiate polymerization. The reaction mixture is stirred to insure good mixing but stopped just before the cloud point of polymerization. The resulting gel is screened through a nylon mesh. The particles are washed with NaHCO$_3$ buffer solution and then lyophilized until dry.

The following examples of the preparation of biologically compatible polymers are presented to further illustrate various embodiments of the present invention. These examples are not to be considered limiting, however, as other biological agents, polymers, initiators, crosslinking agents, and the like, may be used in the practice of the invention.

To test the hemocompatibility properties of the biologically compatible polymers prepared according to the Examples, one or more of the following tests were performed.

Tests For Determining Hemocompatibility of the Prepared Polymers

Thrombin Time: The thrombin time is the time required for formation of a fibrin clot when 3 ml of a 0.3% aqueous solution of fibrinogen is mixed with 0.2 ml of an aqueous solution of thrombin in the presence of a gel containing 1 mg of heparin or in a bicarbonate buffer solution containing 1 mg of heparin.

Blood Clotting Time: The blood clotting time is the time for 5 ml of canine blood to clot in a glass tube at 37° C. in the presence of 2 g of swollen heparin-containing gel or in the presence of 2 g of swollen gel not containing heparin.

Relative Blood Clotting Time (RCT): The relative blood clotting time was the ratio of the clotting time (in a dust-free chamber) of a drop of canine blood on the treated polymeric film to the clotting time of a drop of canine blood on a glass surface.

Measurement of Fibrinolytic Activity: The fibrinolytic activity is measured, as follows. To absorb plasminogen, the swollen particles of trypsin- and lysine-containing gel are incubated with plasma from canine blood for 5 hours. After incubation at 37° C., during which adsorption and activation of plasminogen takes place, 1 ml of gel is placed on the surface of a plate of stabilized fibrin with an area of 3.8 cm$^2$. The stabilized fibrin is obtained by reacting 30 ml of a 0.3% aqueous solution of fibrinogen with 1.8 ml of a 0.4% aqueous solution of thrombin.

The mixture of gel and stabilized fibrin is incubated at 37° C. for about 3 minutes, after which 4 ml of a 0.9% aqueous solution of sodium chloride is added to the mixture. The gel and the remaining fibrin are removed by filtration and the concentration of water-soluble products, as tyrosine, is determined at 279 nm in a UV-spectrometer, employing a previously obtained calibration curve.

Relative Index of Thrombocyte (Platelet) Adhesion (RITA): RITA is the ratio of the number of platelets adhered by a unit surface of the treated polymer and the number of platelets adhered by an equivalent unit of a glass surface. Glass plates or treated polymeric film are incubated with canine blood plasma containing $^{51}$Cr-labelled platelets for 10 minutes at 37° C. and the radioactivity of the surfaces are determined by standard methods. The number of platelets adhered by the unit of glass surface is usually about 500 platelets per $10^{-4}$ cm$^2$.

EXAMPLES

EXAMPLES 1–8

Examples 1–8 illustrate the process of the invention for preparing heparin-containing hemocompatible polymeric gels by copolymerization of heparin, preliminarily acylated by an unsaturated acid chloride, with polymerizable monomers or a mixture of monomers, such as acrylamide, N-vinylpyrrolidone, or a mixture of these with methyl acrylate or methyl methacrylate, in the presence of a radical polymerization initiator, such as riboflavin, asobisisobutyronitrile, a mixture of ammonium persulfate and TMEDA, and the like. Copolymerization was carried out at 0° C.–30° C. To increase the rigidity of the polymeric gel and to reduce its volume in the swelled state, copolymerization was performed in the presence of a crosslinking agent, e.g., N,N'-methylenebisacrylamide. Other crosslinking agents which can be used include, but are not limited to, diesters of acrylic or methacrylic acids, acylated heparin containing two or more double bonds, and the like. Acylation of heparin by acrylic or methacrylic acid chloride was carried out at pH 6.0–9.0, preferably 7.0–8.0, at 0° C. to 30° C., and at a molar ratio of heparin:acid chloride of 1:5–100. When a crosslinking agent was used, the weight ratio of monomer to crosslinking agent was 95:5 to 50:50.

EXAMPLE 1

Heparin was acylated at 0° C. by adding acrylic acid chloride (0.9 g) to a solution of heparin (1.5 g) in 50 ml of bicarbonate buffer at pH 9.0. The molar ratio of heparin to the acid chloride was 1:100. When the entire amount of acid chloride was added, the mixture was stirred for 15 min, followed by the addition of acrylamide (4.75 g) and a solution of N,N'-methylenebisacrylamide (0.25 g). Polymerization was conducted at 0° C. under argon using a mixture of ammonium persulfate and TMEDA as an initiator of radical polymerization. After polymerization was complete (1 hour), the resulting gel was reduced to a small size over nylon sieves and washed with bicarbonate buffer and a 0.6 N solution of NaCl. The content of heparin in the gel was 15 mg per ml of the swelled gel.

The biological activity of the heparin in the gel was tested by measuring the thrombin time and blood clotting time, as described above.

Results: The thrombin time in the presence of the heparin-containing acrylamide gel was 19 seconds. The thrombin time in the presence of 1 mg of heparin in solution was 19 seconds. Therefore, when the thrombin time was measured, the activity of the heparin in the gel was equivalent to the activity of the heparin in solution.

The blood clotting time in the presence of heparin-containing acrylamide gel was greater than 20 minutes. In contrast, the blood clotting time in the presence of acrylamide gel prepared the same way but not containing heparin was 3 to 5 minutes. Therefore, the heparin in the gel retained its anticoagulant activity.

Following the test for blood clotting time employing the heparin-containing gel, the blood was tested for free heparin. No free heparin was found in the blood. Therefore, the anticoagulant activity was due to the heparin contained in the gel.

EXAMPLE 2

Heparin was acylated at 30° C. by adding acrylic acid chloride (0.03 g) to a solution of heparin (1.0 g) in 30 ml of bicarbonate buffer at pH 8.0. The molar ratio of the heparin to the acid chloride was 1:5. When the entire amount of the acid chloride was added, the mixture was stirred for 10 min, followed by the addition of acrylamide (4.75 g) and N,N'-methylenebisacrylamide (0.25 g). Copolymerization was conducted at 30° C. using riboflavin (10 mg/l) as an initiator of radical polymerization. The gel was then sieved and washed as described in Example 1. The content of heparin in gel was 18 mg/ml of the swelled gel. The thrombin time and blood clotting time were measured as described in Example 1. The results showed a thrombin time of 20 sec/mg of heparin in the gel and a blood clotting time of greater than 20 minutes in the presence of the heparin-containing gel.

EXAMPLE 3

Acylation of heparin was performed at 0° C. by adding methacrylic acid chloride (0.034 g) to a solution of heparin (1.0 g) in 50 ml of phosphate buffer at pH 6.0. The mixture was stirred for 15 minutes and acrylamide (30 g) was added. Polymerization was conducted at 20° C. under argon in the presence of asobisisobutyronitrile. The mixture was irradiated with UV radiation for 1 hour. After precipitation with acetone, a white polymer soluble in water and containing 21 mg of heparin/gram of copolymer was obtained. The thrombin time was measured as described in Example 1. The results showed a thrombin time of 18 sec/mg of heparin in the gel.

EXAMPLE 4

Heparin was immobilized as described in Example 3. The time of polymerization was 5 hours. A gel-like copolymer swelled in water was prepared. The content of heparin was 36 mg/ml of the swelled gel.

EXAMPLE 5

Heparin was immobilized as described in Example 1 by adding acrylamide (20 g) and N,N'-methylenebisacrylamide (3 g) to acylated heparin (2.5 g) in 50 ml of bicarbonate buffer. The content of heparin was 24 mg/ml of the swelled gel. The thrombin time was measured as described in Example 1. The results showed a thrombin time of 20 sec/mg of heparin in the gel.

EXAMPLE 6

Heparin was immobilized as described in Example 1 by adding N-vinylpyrrolidone (1 g) and diester of methacrylic acid (1 g) and poly(oxyethylene glycol), with a degree of polymerization equal to 13, to acylated heparin (1.0 g) in 5 ml of bicarbonate buffer. The content of heparin was 75 mg/ml of swelled gel. The blood clotting time in the presence of the heparin-containing gel was greater than 40 minutes.

EXAMPLE 7

Heparin was immobilized as described in Example 2 by adding acrylamide (5 g) and methylmethacrylate (2 g) to a solution of heparin (1.0 g) acylated by acrylic acid chloride in 40 ml of bicarbonate buffer. The copolymer was then swelled in water and had a heparin content of 16 mg/ml of the swelled gel.

EXAMPLE 8

Heparin was immobilized as described in Example 1 by adding acrylamide (7 g) and N,N'-methylenebisacrylamide (1 g) to a solution of acylated heparin (2.0 g) in 10 ml of bicarbonate buffer. The copolymer was then swelled in water and had a heparin content of 80 mg/ml of the swelled gel.

The above Examples 1–8 illustrate that the process for preparing hemocompatible polymeric gels according to the invention makes it possible to obtain preparations containing up to 80 mg of heparin/ml of the swelled gel. In contrast, previous attempts to bind heparin to polymeric gels have reported concentrations of only 11 to 17 mg of heparin/ml of the swelled gel. (See Halpern, B. D. et al., Interac. Liquid at Solid Substr., 87:197 [1968]). In addition, the process of the invention provides heparin-containing polymeric gels in which the specific biological activity of heparin is equivalent to that of heparin in solution.

EXAMPLES 9–16

In the following Examples 9–16, polymeric hydrogels with enhanced hemocompatibility, containing a copolymerized derivative of L-lysine (Nε-methacryloyl-L-lysine) and a copolymerized derivative of trypsin, were prepared. The structure of the L-lysine derivative was:

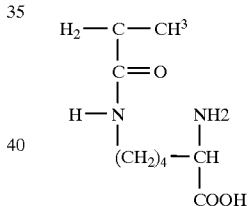

EXAMPLE 9

A solution of trypsin (0.3 g) in 20 ml of bicarbonate buffer (pH 8.0) was treated with acrylic acid chloride (0.0684 g) with intense stirring at 0° C. for 15 min. Then, the mixture was heated to room temperature. Acrylamide (2.97 g), N$^\epsilon$-methacryloyl-L-lysine (0.03 g), N,N'-methylenebisacrylamide (0.15 g), and 20 ml of distilled water were added to the prepared solution. The mixture was purged with argon for 20 minutes and ammonium persulfate and TMEDA were added in the amount of 0.3 wt % of the mixture of monomers. Polymerization was conducted for 1 hour at room temperature. The resulting gel was reduced to small size over nylon sieves, washed with distilled water and a physiologic solution, and allowed to swell in blood plasma for 5 hours. After complete swelling, the biological activity of the lysine/trypsin-containing hydrogel was measured with respect to its fibrinolytic activity its effect on the blood clotting time by the tests described above.

EXAMPLES 10–16

The composition and properties of hydrogel Examples 10–16, prepared as described in Example 9, are shown in Table 1. Example 14 is a gel composition that does not contain the L-lysine derivative. The fibrinolytic activity and the prolongation of the blood clotting time are therefore that due to the trypsin alone. Each of Examples 9–11 illustrates a substantially equivalent increase in fibrinolytic activity and blood clotting time with gels containing 1, 2, and 1.5 weight percentages of the L-lysine derivative. Example 12 illustrates that 0.066 weight percent of the L-lysine derivative is not enough to produce an increase in fibrinolytic activity and blood clotting time; whereas, Example 13 illustrates that 3 weight percent also does not produce these activities. Therefore, there appears to be a limited window of the concentration of the L-lysine derivative that produces the desired effect. Example 16, which illustrates a composition identical to Example 9 except for the use of a different crosslinking agent, shows that the results are reproducible and not dependent on the choice of crosslinking agent.

EXAMPLES 17 AND 18

These examples describe the preparation of a polymeric hydrogel drain for improving the outflow of a fluid from a body cavity and to prevent closure of such a drain by clogging due to thick masses of proteins, blood and other substances that may be in the fluid. Such a drain, for example, could be used for draining exudate from the abdominal cavity in the treatment of peritonitis.

The drain comprises a polymeric hydrogel material having two layers, the internal layer containing heparin and at least one enzyme, preferably including a proteolytic enzyme, to inhibit blood clotting and break down proteinaceous and other materials in the exudate, and further contains an antibiotic to inhibit or kill infectious organisms in the exudate. The outer layer contains at least one enzyme inhibitor, preferably an inhibitor for each enzyme employed in the drain, to prevent attack by the enzyme on the tissue layer surrounding the drain, and an antibiotic to prevent infection due to the drain itself. The weight percentage of the various components may be as follows:

| In the Internal Layer: | |
|---|---|
| Heparin | 0.02–2.0 |
| Enzyme | 0.04–4.0 |
| Antibiotic | 0.001–0.002 |
| In the External Layer: | |
| Enzyme inhibitor | 0.05–2.0 |
| Antibiotic | 0.001–0.002 |

Drain Preparation

EXAMPLE 17

Heparin (0.5 g) was dissolved in 100 ml of bicarbonate buffer and acrylic acid chloride (0.8 ml) was added to the obtained solution. The mixture was stirred for 20 min. A solution in bicarbonate buffer of the proteolytic enzyme, trypsin, was prepared in a similar way employing 1 g of trypsin. A bar with a diameter of 8 mm was placed in an ampule with an inner diameter of 10 mm. A solution containing 0.001 g of the antibiotic kanamycin and an aqueous solution containing 0.05 g of pancreatic trypsin inhibitor was added between the rod and a wall of the ampule. Then, acrylamide (10.0 g) and a crosslinking agent N,N-methylenebisacrylamide (1.0 g) were added. Polymerization was conducted at room temperature for 1 hour. The rod was then removed from the ampule and another rod, with a diameter of 6 mm, was placed in the same ampule. A solution containing 0.001 g kanamycin, 0.02 g acylated heparin, 0.04 g acylated trypsin and 10.0 g acrylamide and 1.0 g N,N-methylenebisacrylamide was placed between the 6 mm rod and the polymeric gel prepared in the first stage. After 1 hour the rod was removed and the drain was removed from the ampule.

EXAMPLE 18

Proteolytic enzyme inhibitor (2.0 g), kanamycin (0.02 g) and acrylic acid chloride (0.8 ml) were added to 100 ml of bicarbonate buffer similarly to that in Example 17. A rod with a diameter of 8 mm was placed in an ampule with an inner diameter of 10 mm. The above solution was added between the rod and a wall of the ampule. Then, acrylamide (10.0 g) and crosslinking agent N,N-methylenebisacrylamide (1.0 g) were added and polymerization was conducted at room temperature for 1 hour. Then, the first rod was removed from the ampule and another rod with a diameter of 6 mm was placed in the same ampule. A solution containing 0.002 g kanamycin, 2.0 g acylated heparin, 4.0 g acylated trypsin and 10.0 g acrylamide and 1.0 g N,N-methylenebisacrylamide was placed between the 6 mm rod and the polymeric gel prepared in the first stage. After 1 hour the rod was removed and the drain was removed from the ampule.

EXAMPLES 19–29

In the following Examples 19–29, polymeric materials were prepared that demonstrate enhanced hemocompatibility due to a decrease in the adhesion of platelets on their surface. The surfaces of the polymeric materials were modified by radiation-induced graft copolymerization with unsaturated derivatives of salicylic acid and adenine. The exemplary derivatives were:

(i) acryloylsalicylic acid (ASA) having the general formula:

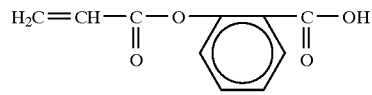

(ii) methacryloyl salicylic acid (MSA) having the general formula:

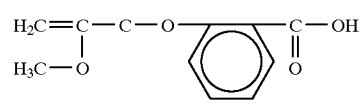

(iii) acryloyladenine (AAD) having the general formula:

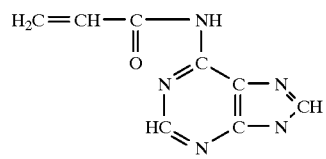

(iv) methacryloyladenine (MAD) having the general formula:

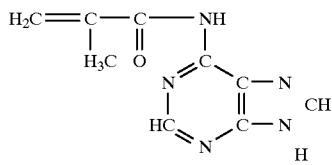

Preparation of Derivatives

Preparation of Acryloylsalicylic Acid (ASA)

Potassium hydroxide (11.2 g, 0.2 mole) was dissolved in 50 ml of methanol and salicylic acid (13.8 g, 0.1 mole) was added. The formed precipitate was separated and dried in vacuum. The precipitate (0.1 mole, 17.6 g) of potassium salicylate was dissolved in 50 ml of benzene, heated to boiling and acryloyl chloride (22.1 g, 0.2 mole) was added with intense stirring for 2 hours. The formed precipitate was centrifuged, the benzene solution was evaporated using a rotor evaporator and the formed solid product, potassium acryloyl salicylate, was dried in a vacuum. The prepared salt (12.8 g, 0.06 mole) was dissolved in 150 ml of distilled water and 150 ml of a 20% solution of trifluoroacetic acid was added. The formed emulsion was stirred for 40 min. Then, 300 ml of diethyl ether was added and the mixture was stirred for 5–6 hours. The ether layer was separated, dried over magnesium sulfate, and evaporated in a vacuum to a dry state. The white precipitate was recrystallized from benzene. The yield of ASA from the mixture was 30%.

The calculated analysis (percent) for the $C_{10}H_8O_4$ was C=62.50; H=4.16; O=33.34. The analysis (percent) of the prepared compound showed C=62.00; H=4.31; O=33.25.

The compound was identified by infrared (IR) spectroscopy, which showed absorption bands at 1610 cm-1 (stretching vibrations of C=C bond) and 1410 cm-1 (in-plane bending vibrations of CH group in —CH=CH$_2$). This pattern unambiguously suggested that an acryloyl group was introduced into the salicylic acid and that the desired ASA compound was synthesized.

Preparation of Methacryloylsalicylic Acid (MSA)

All procedural steps and molar ratios were similar to those described for the preparation of acryloylsalicylic acid. The prepared MSA product was a white powder, with a yield of 45%.

The calculated analysis (percent) for the $C_{11}H_9O_4$ was C=65.02; H=3.44; O=31.54. The analysis (percent) of the prepared compound showed C=65.40; H=3.55; O=32.00. The IR spectra showed bands characteristic of the C=C bond, similar to those of the acryloylsalicylic acid.

Preparation of Acryloyladenine (AAD)

Adenine (0.27 g, 0.002 mole) was dissolved in 7 ml of bicarbonate buffer (pH 8), cooled to 0°–4° C., and acrylic acid chloride (1.1 g, 0.01 mole) was added with intense stirring for 1 hour. The solution was acidified with 1 M HCl until pH 6 was obtained, the solvent was evaporated in vacuum and the formed white precipitate was recrystallized from dimethyl sulfoxide. The yield of the AAD was 70%. The IR spectra displayed no absorption bands at 1650 cm-1 (bending vibrations of NH$_2$ groups); however, absorption bands appeared at 1680 (amide-I), 1540 (amide-II), and 1290 (amide-III). These data confirm that a compound of AAD having the above formula was prepared.

Preparation of Methacryloyladenine (MAD)

All procedural steps and molar ratios were the same as those for the preparation of acryloyladenine, except that methacryloyl chloride was used instead of acryloyl chloride. The yield of MAD was 85%. The IR spectra showed the same bands as the IR spectra of AAD.

The calculated analysis (percent) for the $C_8H_7N_5O$ was C=55.56; H=3.60; N=36.84; O=4.00. Analyses of the prepared AAD compound showed C=53.85; H=2.45; N=34.50; O=9.00, and of the prepared MAD compound ($C_9H_9N_5O$) showed C=55.50; H=2.00; N=34.65; O=8.30.

EXAMPLE 19

Preparation of the ASA Polymeric Hemocompatible Material

Degreased polyethylene film (25 cm$^2$) was placed in a glass ampule. A dilute solution of ASA in water (0.004 mg/cm$^2$ of the film) was added. The solution was degassed, evacuated to the residual pressure of $10^{-3}$ Torr, and the ampule was sealed. The ampule was irradiated by γ-radiation with a dose of 0.5 Mrad/hour. The total dose was 2.5 Mrad/5 hours. After irradiation was complete, the polymeric material was taken from the ampule and washed with a sterile physiologic solution.

EXAMPLES 20–29

The polymeric hemocompatible materials employing ASA, MSA, AAD and MAD were prepared by the procedural steps of Example 19, using the polymeric films and the concentration of the reactants listed in Table 2. Acryloyltrypsin (AT) and acryloylplasmin (AP) were prepared as described for acryloyltrypsin in Example 9. Hemocompatibility of the polymers was determined by the relative clotting time (RCT) and the relative index of thrombocyte adhesion (RITA) tests, as described above. The results of these tests are also reported in Table 2.

Results: As illustrated in the Table, polyethylene film or polyethylene terephthalate film graft copolymerized with a solution containing 0.004 to 0.05 mg/cm$^2$ of an unsaturated derivative of salicylic acid or adenine (ASA, MSA, AAD and MAD), showed significant inhibition of platelet adhesion and prolongation of blood clotting times, compared with untreated polyethylene film or polyethylene film treated with a solution containing less than 0.004 or greater than 0.05 mg/cm$^2$ of the derivative.

Thus, the invention makes it possible to prepare hemocompatible polymeric materials showing enhanced hemocompatibility due to a decrease in adhesion of thrombocytes on their surface.

EXAMPLES 30–37

Examples 30–37 describe the preparation of hemocompatible polymeric materials by radiation-induced graft copolymerization of the polymeric materials with the acid chloride of acrylic or methacrylic acid, followed by treatment of the graft copolymer with an aqueous solution of a biologically active compound. The exemplary biologically active compound was a mixture of heparin and trypsin at a weight ratio of 1 to 3.5:1 from an aqueous solution of 0.3 to 5.0% by weight of heparin and 0.2–1.0 % by weight of trypsin.

The process involved two stages. In the first stage, the acid chloride of acrylic or methacrylic acid was grafted onto a polymer from a gas phase at a γ radiation dose of 1.0 to 4 Mrad. The choice of this dose range was determined by the observation that at doses less than 1.0 Mrad, the effective amount of the grafting of the acid chloride was low (15–20 weight % based on the weight of the polymer), which was found to be an insufficient degree of grafting for a successful stage two. At doses of γ radiation greater than 4.0 Mrad, degradation of the polymers occurred. The optimum radiation dose must be determined for each polymer and is dependent upon the chemical nature of the polymer. For example, the radiation doses for the same polymer in film, powder or fiber form, differ significantly.

Generally speaking, the dose of radiation must be sufficient to result in a graft copolymer having at least 25 weight % of the substrate polymer grafted and preferably at least 35 and up to 90 weight % but below the dose that appreciably degrades the polymer (e.g. above 5% and preferably below 2% weight %). Those skilled in the art may easily determine the appropriate range of radiation for a specific polymer in a particular form.

At the second stage, the graft copolymer was treated with a solution of a heparin-trypsin mixture with a concentration of 30–50 mg/ml heparin and 2–10 mg/ml trypsin, at a ratio of heparin:trypsin of 1–3.5:1. The choice of the concentration ranges was determined by the observations that (i) the amount of heparin bound to the polymer surface (0.3–0.5 mg/cm$^2$) did not increase with higher solution concentrations, and (ii) an amount of trypsin less than 0.1 mg/cm$^2$ on the surface did not impart proteolytic activity to the grafted film.

The treatment of the graft copolymer with the aqueous solution of the heparin:trypsin mixture was performed by immersing the polymeric materials in the solution at 0°–4° C. for 10–14 hours.

The hemocompatibility of the treated polymeric materials prepared as described in Examples 30–34 below was determined by the relative blood clotting time (RCT) and RITA, as described above. The results of the testing are illustrated in Table 3. The prepared polymeric materials show a prolonged blood clotting time, a reduced relative index of thrombocyte adhesion, and the capability of lysing clots of stabilized fibrin.

EXAMPLE 30

Degreased polyethylene film with a surface area of 80 cm$^2$ was placed in an ampule such that the film was stretched on the bottom of the ampule over 1 ml of acrylic acid chloride. The ampule was evacuated to a pressure of 10$^{-3}$ torr, sealed and irradiated with γ-radiation from a $^{60}$Co source at 0.5 Mrad/hour, for a total dose of 1.5 Mrad. Following irradiation, the ampule was opened, the film was washed with absolute ether and immersed for 12 hours at 4° C. in a solution containing 105 mg heparin and 105 mg trypsin in 350 ml bicarbonate buffer. The ratio of heparin to trypsin was 1:1. The entire surface of the film was covered with the solution. After the immersion was completed, the grafted film was washed with a buffer, distilled water, and a physiologic solution until the absorption of the wash water at 280 or 220 nm disappeared, as determined by spectrophotometry.

As illustrated in Table 3, the amount of heparin immobilized on the film was determined to be 0.31 mg/cm$^2$ and the amount of immobilized trypsin immobilized on the film was determined to be 0.16 mg/cm$^2$, or a weight ratio of heparin:trypsin of 1.9:1. The relative time of blood clotting on the prepared film was 2.1±0.3 and the relative index of thrombocyte adhesion was 2.3±0.7.

The following Examples 31–35 illustrate polyethylene film grafted with heparin and trypsin at varying ratios, with trypsin alone, with heparin alone, and unmodified polyethylene film. The concentrations of these compounds and the results of hemocompatibility testing are illustrated in Table 3.

EXAMPLE 31

Polyethylene film grafted with heparin and trypsin at a beginning ratio of 2:1 was prepared by the method described in Example 30.

EXAMPLE 32

Polyethylene film grafted with heparin and trypsin at a beginning ratio of 3:1 was prepared by the method described in Example 30.

EXAMPLE 33

Polyethylene film grafted with trypsin only was prepared by the method described in Example 30.

EXAMPLE 34

Polyethylene film grafted with heparin only was prepared by the method described in Example 30.

EXAMPLE 35

Polyethylene film was prepared by the method described in Example 30 without exposure to heparin or trypsin.

EXAMPLES 36–42

These examples illustrate biologically compatible polymer films prepared by radiation-induced graft copolymerization of polymeric material (i.e. polyethylene, polypropylene, poly(methyl methacrylate), cellulose and polyurethane) with acrylic or methacrylic acid chloride followed by treatment of the graft copolymer with an aqueous solution of a biologically active compound (e.g. heparin and trypsin) that enhances the hemocompatibility of the polymeric materials.

EXAMPLE 36

Acid chloride of methacrylic acid was grafted onto a polyethylene film with a surface area of 36.4 cm$^2$ by the method described in Example 30. The graft polymer was treated with a heparin-trypsin mixture at a ratio of heparin:trypsin of 1.2:1. The results of testing for the relative time of blood clotting and relative index of thrombocyte adhesion are presented in Table 4.

EXAMPLES 37–42

Hemocompatible polymeric films were grafted with heparin and trypsin according to the method described in Example 36. The results of hemocompatibility testing are presented in Table 4. The prepared polymeric materials show an extended time of blood clotting, a reduced relative index of thrombocyte adhesion, and the capability of lysing clots of stabilized fibrin.

While the invention has been described herein with reference to the preferred embodiments, it is to be understood that it is not intended to limit the invention to the specific forms disclosed. On the contrary, it is intended to cover all modifications and alternative forms falling within the spirit and scope of the invention.

TABLE 1

| Example Number | COMPOSITION OF REACTION MIXTURE | | | | | | | | HEMO-COMPATIBILITY | |
|---|---|---|---|---|---|---|---|---|---|---|
| | Trypsin (g) | AAC$^a$ (g) | Acrylamide (g) | weight % | MAL$^2$ (g) | weight % | Cross-linking agent (g) | Water (ml) | Fibrinolytic Activity µg tyrosine/min per 1 ml of gel | Blood Clotting Time (min) |
| 9$^3$ | 0.30 | 0.0684 | 2.97 | 99.0 | 0.03 | 1.00 | 0.15 | 40 | 31 ± 2 | 134 ± 3 |
| 10$^3$ | 0.18 | 0.0456 | 2.94 | 98.0 | 0.06 | 2.00 | 0.30 | 30 | 36 ± 3 | 127 ± 3 |
| 11$^3$ | 0.07 | 0.1090 | 3.28 | 98.5 | 0.05 | 1.50 | 0.20 | 30 | 33 ± 3 | 130 ± 3 |
| 12$^3$ | 0.30 | 0.3420 | 2.98 | 99.4 | 0.02 | 0.066 | 0.15 | 36 | 11 ± 1 | 35 ± 1 |
| 13$^3$ | 0.20 | 0.0218 | 2.91 | 97.0 | 0.09 | 3.00 | 0.15 | 40 | 10 ± 1 | 30 ± 1 |
| 14$^3$ | 0.30 | 0.0684 | 3.00 | 100 | — | — | 0.15 | 40 | 6 ± 0.15 | 33 ± 1 |
| 15$^3$ | 0.90 | 0.0684 | 2.97 | 99.0 | 0.03 | 1.00 | 0.15 | 40 | 34 ± 3 | 134 ± 2 |
| 16$^4$ | 0.30 | 0.0684 | 2.97 | 99.0 | 0.03 | 1.00 | 0.15 | 40 | 33 ± 3 | 126 ± 3 |

$^1$ACC is acrylic or methacrylic acid chloride.
$^2$MAL is N$^6$-methacryloyl-L-lysine
$^3$N,N-methylenebisacrylamide is used as crosslinking agent.
$^4$Tridecaethyiene glycol dimethacrylate (TGM-13) is used as crosslinking agent.

TABLE 2

| Example Number | Polymeric Material (film) | UBAC$^1$ | Amount of UBAC per 1 cm$^2$ of polymer surface (mg. in solution) | Relative Blood Clotting Time Time ± 0.3 | Relative Index of Thrombocyte Adhesion, +/− 0.1 |
|---|---|---|---|---|---|
| 19 | polyethylene | ASA$^2$ | 0.004 | 1.5 | 0.8 |
| 20 | polyethylene | MSA$^3$ | 0.008 | 1.6 | 0.7 |
| 21 | polyethylene-terephthalate | AAD$^4$ | 0.050 | 1.4 | 0.8 |
| 22 | polyethylene-terephthalate | MAD$^5$ | 0.010 | 1.6 | 0.8 |
| 23 | polyethylene | ASA | 0.003 | 1.2 | 3.6 |
| 24 | polyethylene | AAD | 0.060 | 1.4 | 2.7 |
| 25 | polyethylene | ASA | 0 | 1.0 | 4.7 |
| 26 | polyethylene | AAD | 0 | 1.1 | 5.6 |
| 27 | polyethylene | AT$^6$ | 0.010 | 1.2 | 4.5 |
| 28 | polyethylene | AP$^7$ | 0.050 | 1.4 | >3.0 |
| 29 | polyethylene | | | 1.1 | 1.3 |

$^1$UBAC = Unsaturated derivative of biologically active compound.
$^2$ASA = Acryloylsalicylic acid.
$^3$MSA = Methacryloylsalicylic acid.
$^4$AAD = Acryloyladenine.
$^5$MAD = Methacryloyladenine.
$^6$AT = Acryloyltrypsin.
$^7$AP = Acryloylplasmin.

TABLE 3

| Example Number | Polymeric Material | Amount of Heparin in Mixture (solution) mg | Amount of Trypsin in Mixture (solution) mg | Amount of Immobilized Heparin mg/cm$^2$ | Amount of Immobilized Trypsin mg/cm$^2$ | Weight Ratio Heparin/Trypsin | RCT* | RITA** |
|---|---|---|---|---|---|---|---|---|
| 30 | PE$^1$ film | 105 | 105 | 0.31 | 0.16 | 1.9 | 2.1 ± 0.3 | 2.3 ± 0.7 |
| 31 | PE film | 210 | 105 | 0.47 | 0.11 | 4.2 | 1.7 ± 0.3 | 3.4 ± 1.1 |
| 32 | PE film | 315 | 105 | 0.307 | 0.257 | 1.2 | 3.22 ± 0.3 | 1.6 ± 0.5 |
| 33 | PE film | — | 105 | — | 0.14 | — | 1.2 ± 0.1 | 1.3 ± 0.5 |
| 35 | PE film (modified) | — | — | — | — | — | 1.2 ± 0.1 | 1.8 ± 0.5 |

*RCT = Relative Blood Clotting Time.
**RITA = Relative Index of Thrombocyte Adhesion.
$^1$PE = Polyethylene

TABLE 4

| Example Number | Polymer | Acid chloride | Weight Ratio Heparin: Trypsin in Solution | Degree of Grafting wt % | RCT* | RITA** |
|---|---|---|---|---|---|---|
| 36 | Polyethylene | Methacrylic acid chloride | 1.2:1 | 70.3 | 1.6 | 1.2 |
| 37 | Polyethylene | Acrylic acid chloride | 1.9:1 | 37.8 | 2.1 | 1.2 |
| 38 | Polyethylene | Methacrylic acid chloride | 2.0:1 | 30.0 | 2.2 | 1.4 |
| 39 | Poly(methyl methacrylate) | Acrylic acid chloride | 3.4:1 | 49.7 | 1.9 | 1.5 |
| 40 | Poly(methyl methacrylate) | Methacrylic acid chloride | 3.4:1 | 50.0 | 1.9 | 1.5 |
| 41 | Cellulose | Acrylic acid chloride | 2.7:1 | 44.5 | 2.5 | 1.3 |
| 42 | Polyurethane | Methacrylic acid chloride | 3.5:1 | 28.6 | 2.2 | 1.7 |

*RCT = Relative Blood Clotting Time.
**RITA = Relative Index of Thrombocyte Adhesion.

What is claimed is:

1. A method for preparing a hemocompatible hydrogel composition comprising:
   (1) functionalizing two or more individual pharmacologic agents by reacting said agents with an unsaturated acyl halide; and
   (2) either:
      copolymerizing said functionalized agents with at least one comonomer to form a hydrophilic polymer and thereafter crosslinking the polymer with a multifunctional crosslinking agent; or
      copolymerizing said functionalized agents with at least one comonomer and at least one multifunctional crosslinking agent to form a crosslinked hydrophilic polymer; or
      grafting said functionalized agents onto a preformed hydrophilic or hydrophobic polymer;
   step (2) being conducted under conditions which result in the production of a hydrogel network to whose backbone said pharmacologic agents are covalently bonded and wherein said agents retain their individual activities upon exposure of said hydrogel composition to blood.

2. The method of claim 1 wherein said acyl halide is an acyl chloride.

3. The method of claim 1 wherein said hemocompatible hydrogel composition is prepared by copolymerizing said functionalized agents with at least one comonomer to form a hydrophilic polymer and thereafter crosslinking the polymer with a multifunctional crosslinking agent.

4. The method of claim 3 wherein said multifunctional crosslinking agent is a polyene.

5. The method of claim 3 wherein said agents are selected from the group consisting of heparin, L-lysine, salicylic acid, enzymes, enzyme inhibitors, antibiotics, and combinations thereof.

6. The method of claim 1 wherein the hemocompatible hydrogel composition is prepared by copolymerizing said functionalized agents with a least one comonomer and at least one multifunctional crosslinking agent to form a crosslinked hydrophilic polymer.

7. The method of claim 6 wherein the multifunctional crosslinking agent is a polyene.

8. The method of claim 6 wherein said agents are selected from the group consisting of heparin, L-lysine, salicylic acid, enzymes, enzyme inhibitors, antibiotics and combinations thereof.

9. The method of claim 1 wherein the hemocompatible hydrogel composition is prepared by grafting said functionalized agents onto a preformed hydrophilic or hydrophobic polymer.

10. The method of claim 9 wherein said agents are selected from the group consisting of heparin, L-lysine, salicylic acid, enzymes, enzyme inhibitors, antibiotics and combinations thereof.

11. A hemocompatible hydrogel composition prepared by a method comprising:
   (1) functionalizing two or more individual pharmacologic agents by reacting said agents with an unsaturated acyl halide; and
   (2) either
      copolymerizing said functionalized agents with at least one comonomer to form a hydrophilic polymer and thereafter crosslinking the polymer with a multifunctional crosslinking agent; or
      copolymerizing said functionalized agents with at least one comonomer and at least one multifunctional crosslinking agent to form a crosslinked hydrophilic polymer; or
      grafting said functionalized agents onto a preformed hydrophilic or hydrophobic polymer;
   step (2) being conducted under conditions which result in the production of a hydrogel network to whose backbone said pharmacologic agents are covalently bonded and wherein said agents retain their individual activities upon exposure of said hydrogel composition to blood.

12. The composition of claim 11 wherein said agents are selected from the group consisting of heparin, L-lysine, salicylic acid, enzymes, enzyme inhibitors, antibiotics and combinations thereof.

13. An article of manufacture having opposing surfaces made from a hemocompatible hydrogel composition prepared by the method of claim 3, 6, or 9.

14. An article of manufacture having at least one surface which has been coated with the hemocompatible hydrogel composition of claim 11.

15. The article of manufacture of claim 14 wherein the coated surface is a metal.

16. A hemocompatible hydrogel composition produced by the method of claim 1, wherein the acyl halide is an acyl chloride and said agents are selected from the group consisting of heparin, L-lysine, plasmin, adenine, salicylic acid, enzymes, enzyme inhibitors, antibiotics and combinations thereof.

17. A composition produced by the method of claim 1, wherein said preformed polymer is irradiated prior to grafting.

18. The composition of claim 17 wherein said agents are selected from the group consisting of heparin, L-lysine, salicylic acid, enzymes, enzyme inhibitors, antibiotics and combinations thereof.

19. The composition of claim 17, wherein said agents are heparin and trypsin.

20. The composition of claim 17, wherein said agents are N-lysine and trypsin.

21. The composition of claim 17, wherein said agents are trypsin and plasmin.

22. The composition of 17, wherein said agents are L-lysine and adenine.

23. The composition of claim 17, wherein said agents are salicylic acid and at least one of adenine, trypsin, plasmin or heparin.

24. The composition of claim 17, wherein said agents are an amino acid and a proteolytic enzyme inhibitor.

25. The composition of claim 24, wherein the amino acid is L-lysine and the inhibitor is a trypsin inhibitor.

26. The composition of claim 17, wherein said agents are heparin and an antibiotic.

27. The composition of claim 17, wherein the dose of radiation is sufficient to graft at least 25 weight percent of the polymer, but not sufficient to degrade same.

28. A medical device wherein at least one part of said device comprises a hemocompatible hydrogel composition produced by the method of claim 1, 5 or 7.

29. The method of claim 1 wherein said preformed polymer is a hydrophilic polymer.

30. The method of claim 29, wherein the polymer is an acrylamide homopolymer or copolymer and said agents are selected from the group consisting of heparin, L-lysine, salicylic acid, enzymes, enzyme inhibitors, antibiotics and combinations thereof.

31. The method of claim 1 wherein said preformed polymer is a hydrophobic polymer.

32. The method of claim 31 wherein said agents are selected from the group consisting of heparin, L-lysine, salicylic acid, enzymes, enzyme inhibitors, antibiotics and combinations thereof.

33. The article of manufacture of claim 14, where the coated surface is a metal or a polymer.

* * * * *